United States Patent [19]

Effland et al.

[11] Patent Number: 4,865,764
[45] Date of Patent: Sep. 12, 1989

[54] 5-ARYL-11-SUBSTITUTED-5H,11H-PYRROLO[2,1-][1,4]BENZOXAZEPINES AS HYPOTENSIVE AGENTS

[75] Inventors: Richard C. Effland; Kevin J. Kapples, both of Bridgewater, N.J.

[73] Assignee: Hoechst-Roussel Pharmaceuticals, Inc., Somerville, N.J.

[21] Appl. No.: 255,300

[22] Filed: Oct. 11, 1988

Related U.S. Application Data

[62] Division of Ser. No. 75,463, Jul. 20, 1987, Pat. No. 4,794,110.

[51] Int. Cl.⁴ .................. C07D 498/04; A61K 31/55
[52] U.S. Cl. ................................................. 514/211
[58] Field of Search ................ 540/547, 511; 514/211

[56] References Cited

U.S. PATENT DOCUMENTS

| | | | |
|---|---|---|---|
| 4,029,672 | 6/1977 | Effland et al. | 514/211 |
| 4,045,448 | 8/1977 | Effland et al. | 514/93 T |
| 4,053,599 | 10/1977 | Effland et al. | 514/211 |
| 4,608,374 | 8/1986 | Effland et al. | 514/211 |
| 4,681,879 | 7/1987 | Effland et al. | 514/211 |

Primary Examiner—Richard A. Schwartz
Assistant Examiner—Finna Northington
Attorney, Agent, or Firm—Tatsuya Ikeda

[57] ABSTRACT

There are disclosed compounds of the formula,

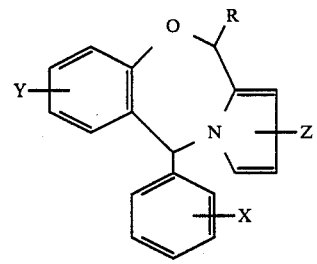

where X and Y are each independently hydrogen, loweralkyl, halogen or trifluoromethyl; Z is hydrogen or 2- or 3-Cl, Br, I, CHO or CH=CR₁R₂ where R₁ and R₂ are each independently hydrogen or loweralkyl; R is hydrogen,

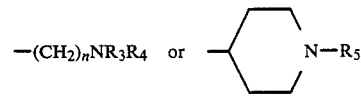

where n is 1, 2 or 3, R₃ is loweralkyl, and R₄ is hydrogen or loweralkyl, or alternatively the group —NR₃R₄ as a whole is

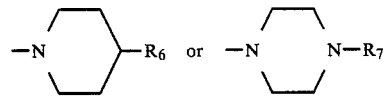

where R₆ is loweralkyl,

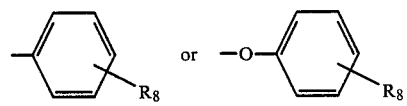

and R₇ is loweralkyl or

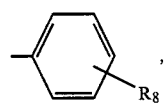

R₈ being hydrogen, loweralkyl, halogen, trifluoromethyl or methoxy; and R₅ is hydrogen, loweralkyl or arylloweralkyl.

2 Claims, No Drawings

5-ARYL-11-SUBSTITUTED-5H,11H-PYRROLO[2,1-][1,4]BENZOXAZEPINES AS HYPOTENSIVE AGENTS

This is a division of a prior application, Ser. No. 075,463, filed July 20, 1987, now U.S. Pat. No. 4,794,110.

The present invention relates to compounds of the formula,

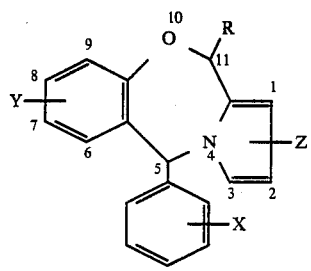

where X and Y are each independently hydrogen, loweralkyl, halogen or trifluoromethyl; Z is hydrogen or 2- or 3-Cl, Br, I, CHO or CH=CR₁R₂ where R₁ and R₂ are each independently hydrogen or loweralkyl; R is hydrogen,

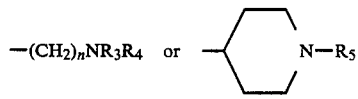

where n is 1, 2 or 3, R₃ is loweralkyl, and R₄ is hydrogen or loweralkyl, or alternatively the group —NR₃R₄ as a whole is

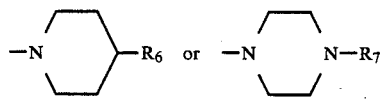

where R₆ is loweralkyl,

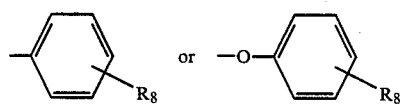

and R₇ is loweralkyl or

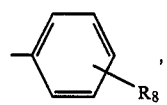

R₈ being hydrogen, loweralkyl, halogen, trifluoromethyl or methoxy; and R₅ is hydrogen, loweralkyl or arylloweralkyl and pharmaceutically acceptable acid addition salts thereof, which are useful as analgesic and hypotensive agents.

Throughout the specification and appended claims, a given chemical formula or name shall encompass all stereo, optical and geometrical isomers thereof where such isomers exist, as well as pharmaceutically acceptable acid addition salts thereof and solvates thereof such as for instance hydrates.

The following general rules of terminology shall apply throughout the specification and the appended claims.

Unless otherwise stated or indicated, the term loweralkyl denotes a straight or branched alkyl group having from 1 to 6 carbon atoms. Examples of said loweralkyl group include methyl, ethyl, n-propyl, iso-propyl, n-butyl, iso-butyl, sec-butyl, t-butyl and straight- and branched-chain pentyl and hexyl.

Unless otherwise stated or indicated, the term loweralkoxy denotes a straight or branched alkoxy group having from 1 to 6 carbon atoms. Examples of said loweralkoxy include methoxy, ethoxy, n-propoxy, iso-propoxy, n-butoxy, iso-butoxy, sec-butoxy, t-butoxy and straight- and branched-chain pentoxy and hexoxy.

Unless otherwise stated or indicated, the term halogen shall means fluorine, chlorine, bromine or iodine.

Unless otherwise stated or indicated the term aryl shall mean a phenyl group having 0, 1, 2 or 3 substituents each of which being independently loweralkyl, loweralkoxy, halogen or CF₃, and the term diaryl shall mean two such aryl groups each of which being independent of the other.

The compounds of this invention are prepared by following one or more of the steps described below. Throughout the description of the synthetic steps, the definitions of X, Y, Z and R are as given above unless otherwise stated or indicated.

STEP A

A compound of formula II is reacted with 2,5-dimethoxytetrahydrofuran to afford a compound of formula III.

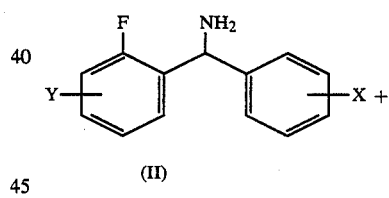

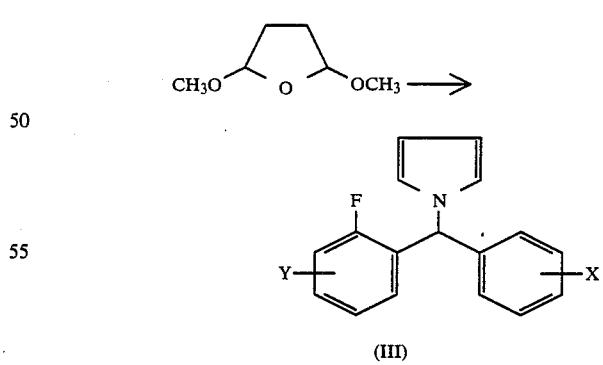

Said reaction is conducted in a suitable medium such as acetic acid at a temperature of about 80° to 120° C. Reflux condition is preferred.

STEP B

Compound III is reacted with chloroacetonitrile to afford a compound of formula IV (Hoeben-Hoesch reaction).

(III) + NCCH₂Cl ⟶ 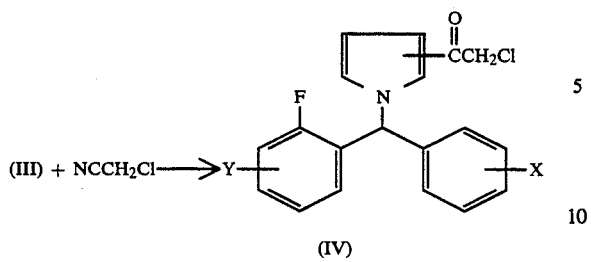

This reaction is typically conducted in a suitable solvent such as diethyl ether, saturating the reaction mixture with hydrogen chloride at a temperature of about 0° to 25° C. to form the corresponding ketimine and subsequently hydrolyzing the latter to obtain said compound IV at a temperature of about 25° to 100° C.

STEP C

Compound IV is reacted with an amine of the formula HNR₃R₄, where R₃ and R₄ are the same as defined earlier except that R₄ may not be hydrogen, to afford a compound of formula V.

(IV) + HNR₃R₄ ⟶ 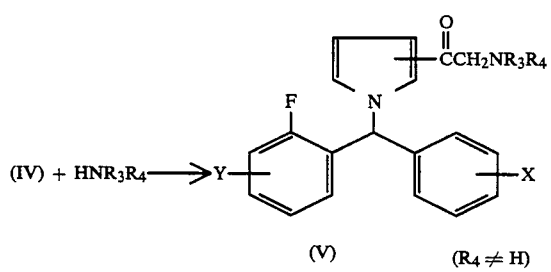

STEP D

Compound V is reduced with NaBH₄ in a manner known to the art to afford a compound of formula VI. Typically said reduction is conducted in a suitable solvent such as isopropanol at a temperature of 25° to 78° C.

(V) + NaBH₄ ⟶ 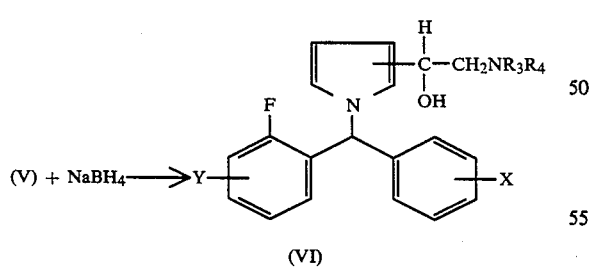

STEP E

Compound III is reacted with phosphorus oxychloride and dimethylformamide (DMF) in a manner known to the art to afford a compound of formula VII (Vilsmeier reaction).

(III) + POCl₃ + DMF ⟶ 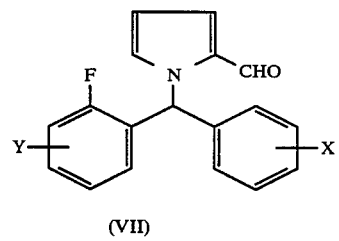

STEP F

Compound VII is converted to the corresponding dithiane of formula VIII by reaction with 2,3-propanedithiol conducted in a manner known to the art, compound VIII is reacted with nBuLi and a compound of the formula ClCH₂CH₂NR₃R₄, where R₄ is not hydrogen, followed by hydrolysis in a routine manner known to the art to afford a compound of formula IX, and the latter is reduced with NaBH₄ is substantially the same manner as in STEP D to afford a compound of formula X.

(VII) $\xrightarrow{\text{HS(CH}_2\text{)}_3\text{SH}}$

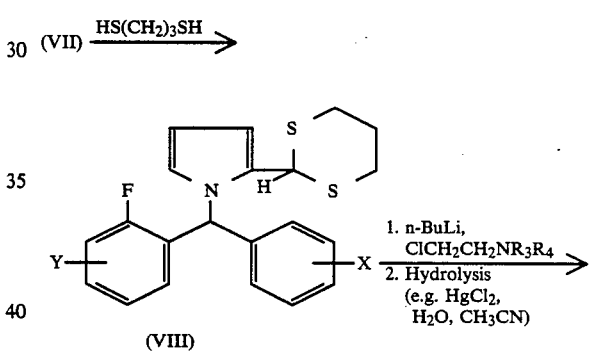

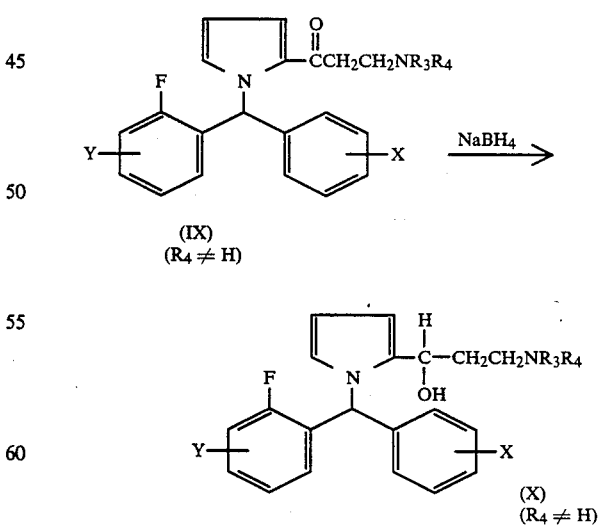

STEP G

Compound VII is reacted with a Grignard reagent of the formula Br-Mg-R₉ where R₉ is

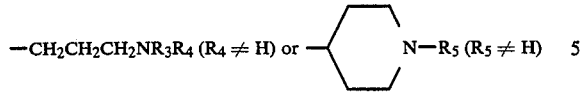

in a routine manner known to the art to afford a compound of formula XI.

(VII) + Br—Mg—R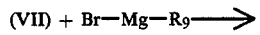

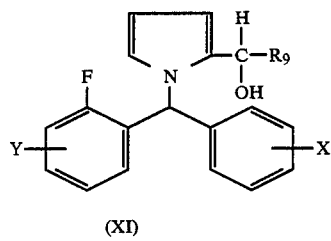

(XI)

STEP H

Compound VII is reduced with NaBH₄ in substantially the same manner as in STEP D to afford a compound of formula XII.

(VII) + NaBH₄ ⟶ 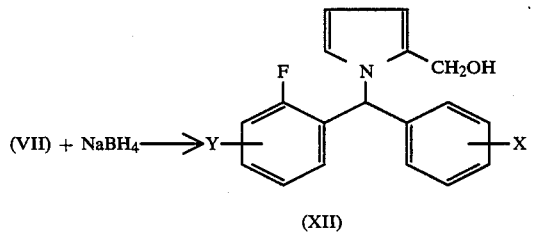

(XII)

STEP I

A compound of formula XIII (where the R is as defined earlier except that it may not contain a secondary amino hydrogen) which is obtained from STEP D, F, G or H is cyclized to afford a compound of formula XIV.

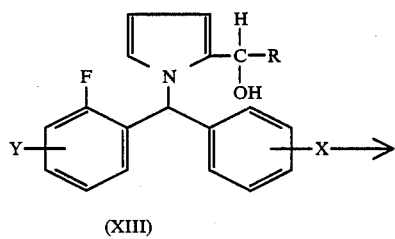

(XIII)

-continued

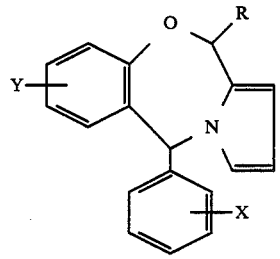

(XIV)

STEP J

Where a compound of formula XIV in which the group R contains a secondary amino hydrogen (namely, when R is $-(CH_2)_n NHR_3$ or 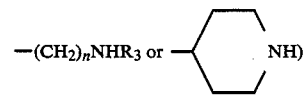

is desired, such a compound can readily be obtained by reacting the corresponding N-methyl compound with ethoxycarbonyl chloride to obtain a carbamate and thereafter hydrolyzing the latter. Thus, for instance, the group

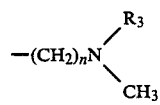

can readily be converted to the group

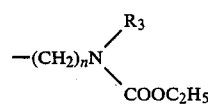

and the latter readily hydrolyzed to $-(CH_2)_n NHR_3$.

STEP K

Compound XIV is reacted with N-chlorosuccinimide, N-bromosuccinimide or N-iodosuccinimide to afford, respectively, a choro, bromo or iodo compound of formula XV where the substituent is at the 2- or 3-position. Positional isomers can usually be separated by use of known techniques such as chromatography or recystallization.

(XIV) + NCS, NBS or NIS ⟶

-continued

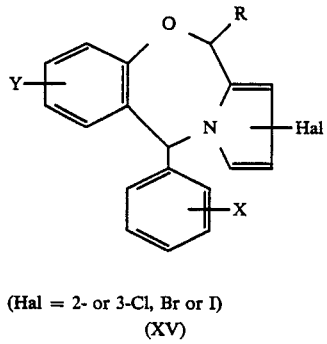

(Hal = 2- or 3-Cl, Br or I)
(XV)

STEP L

Compound XIV is subjected to Vilsmeier reaction in substantially the same manner as in STEP E to afford a 2- or 3-formyl compound of formula XVI.

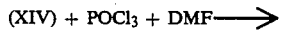
(XIV) + POCl$_3$ + DMF⟶

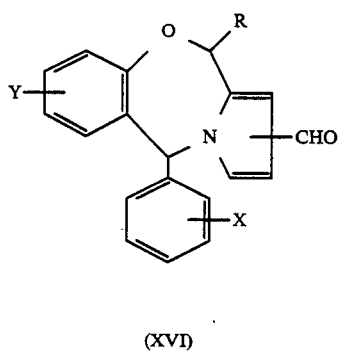

(XVI)

STEP M

Compound XVI is subjected to Wittig reaction with an ylide of the formula $(C_6H_5)_3P=CR_1R_2$ to afford a compound of formula XVII where the substituent —CH=CR$_1$R$_2$ is at the 2- or 3-position.

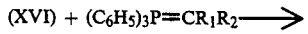
(XVI) + $(C_6H_5)_3P=CR_1R_2$⟶

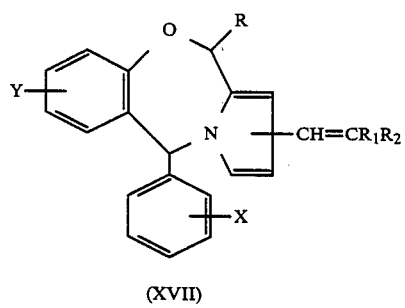

(XVII)

The above reaction can be conducted under conditions usually used for carrying out Wittig reactions. Thus, the ylide is prepared in a routine manner by first preparing a phosphonium salt from a bromide of the formula Br—CHR$_1$R$_2$ and triphenylphosphine and thereafter reacting the phosphonium salt with a suitable base such as sodium hydride, potassium tert-butoxide or n-butyllithium in a suitable solvent such as anhydous ethereal solvent. Thereafter a solution of compound XVI in a suitable solvent such as anhydrous ether is added to the freshly prepared ylide solution and the mixture is stirred at a temperature of between about −10° C. and 80° C.

The compounds of formula I of the present invention are useful as analgesic agents due to their ability to alleviate pain in mammals. The activity of the compound is demonstrated in the 2-phenyl-1,4-benzoquinone-induced writhing test in mice, a standard assay for analgesia [Proc. Soc. Exptl. Biol. Med., 95, 729 (1957)]. Table 1 shows a result of the test of the analgesic activities of some of the compounds of this invention.

TABLE 1

| Compound | ANALGESIC ACTIVITY (Phenylquinone Writhing) Analgesic PQW, % Inhibition of Writhing at 20 mg/kg, s.c. |
|---|---|
| 11-dimethylaminomethyl-5-phenyl-5H,11H—pyrrolo[2,1-c][1,4]benzoxazepine hydrochloride (diasteromer A) | 24 |
| 11-dimethylaminomethyl-5-phenyl-5H,11H—pyrrolo[2,1-c][1,4]benzoxazepine hydrochloride (diasteromer B) | 35 |
| 11-[1-benzylpiperidin-4-yl]-5-phenyl-5H,11H—pyrrolo[2,1-c][1,4]benzoxazepine oxalate (reference compound) | 34 |
| propoxyphene | 50% at 3.9 mg/kg s.c. |

The compounds of formula I of the present invention are also useful as antihypertensive agents due to their ability to depress blood pressure in mammals. Antihypertensive activity is measured in the spontaneous hypertensive rat by the indirect tail cuff method described in "Methods in Pharmacology", A. Schwartz, Ed., Vol. I, Appleton-Century Crofts, New York, N. Y. 1971, p. 135. In this procedure a group of five animals are treated orally for three days with the test compound in relation to a control group of the same number. The drop in blood pressure is measured on the third day following administration. The antihypertensive activities of some of the compounds of this invention, expressed as a decrease in mean arterial blood pressure (in mm Hg), are given in Table 2.

TABLE 2

| Compound | ANTIHYPERTENSIVE ACTIVITY Decrease in Blood Pressure mm Hg at 3 mg/kg, p.o. |
|---|---|
| 11-[1-benzylpiperidin-4-yl]-5-phenyl-5H,11H—pyrrolo[2,1-c][1,4]benzoxazepine oxalate (reference compound) | 44 |
| captopril | 33 at 10 mg/kg p.o. |

Effective quantities of the compounds of the invention may be administered to a patient by any of the various methods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable acid addition salts for purposes of stablity, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compound, but may be varied depending upon the particular form and may conveniently be between 5% to about 70% of the weight of the unit. The amount of active compound in such composition is such that a suitable dosage will be obtained. Preferred compositions and preparations according to the present invention are prepared so that an oral dosage unit form contains between 1.0–300 milligrams of active compound.

The tablets, pills, capsules, troches and the like may also contain the following ingredients: a binder such as micro-crystalline cellulose, gum tragacanth or gelatin; an excipient such as starch or lactose, a disintegrating agent such as alginic acid, Primogel, cornstarch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes, coloring and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of active compound, but may be varied between 0.5 and 30% of the weight thereof. The amount of active compound in such compositions is such that a suitable dosage will be obtained. Preferred compositions and preparations according to the present invention are prepared so that a parenteral dosage unit contains between 0.5 and 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates; citrates or phosphates and agents for the adjustment of tonicity such as sodium chloride or dextrose. The parenteral multiple dose vials made of glass or plastic.

Examples of the compounds of this invention include:
11-dimethylaminomethyl-5-phenyl-5H,11H-pyrrolo[2,1-c][1,4]-benzoxazepine;
11-methylaminomethyl-5-phenyl-5H,11H-pyrrolo[2,1-c][1,4]-benzoxazepine;
11-(1-methyl-4-piperidinyl)-5-phenyl-5H,11H-pyrrolo[2,1-c][1,4]-benzoxazepine; and
11-(1-benzyl-4-piperidinyl)-5-phenyl-5H,11H-pyrrolo[2,1-c][1,4]-benzoxazepine.

The following examples are presented in order to illustrate the present invention.

EXAMPLE 1

1-[2-Fluorophenyl)phenylmethyl]pyrrole

To 100 ml of cooled (0° C.) acetic acid was added α-(2-fluorophenyl)benzenemethanamine (13.09 g). This mixture was then brought to room temperature and 2,5-dimethoxytetrahydrofuran (8.60 g) was added dropwise. The mixture was heated at reflux for 1.5 hours, after which time TLC (thin layer chromatography) showed absence of amine. The mixture was cooled and most of the acetic acid was removed by evaporation. The mixture was dissolved in ether and washed ($3 \times H_2O$; 1 x sat. $NaHCO_3$), dried (sat. NaCl and anhydrous $MgSO_4$), filtered and concentrated to yield a brown solid. Distillation (117° C. @0.15 mmHg) gave a slightly yellow solid (11.33 g). A sample was recrystallized from acetonitrile to give a white crystal, mp 81°–82.5° C.

ANALYSIS: Calculated for $C_{17}H_{14}FN$: 81.25% C; 5.62% C; 5.57% N. Found: 81.02% C; 5.51% C; 5.71% N.

EXAMPLE 2 1

1-[(2-Fluorophenyl)phenylmethyl]pyrrole-2-carboxaldehyde

To cooled (0° C.) dimethylformamide (2.92 g) was added phosphorus oxychloride (6.13 g). This was stirred for 20 minutes causing formation of a thick golden oil. The reaction mixture was brought to room temperature and dissolved in 35 ml of 1,2-dichloroethane (DCE). 1-[(2-Fluorophenyl)phenylmethyl]-pyrrole (10 g) was dissolved in 80 ml of DCE and added dropwise to the stirred solution. The mixture was heated to reflux and stirred for 3.5 hours. TLC showed absence of pyrrole. The reaction mixture was cooled and a solution prepared from 30 g NaOAc·$3H_2O$ dissolved in 75 ml $H_2O$ was added and the reaction mixture was refluxed for one hour. The aqueous layer was separated and extracted with ether. The combined organic layer was washed with water ($2 \times$) and dried with sat. NaCl and anhydrous $MgSO_4$.

The mixture was filtered and the filtrate concentrated to a dark yellow oil. It was purified by column chromatography using methylene chloride as the eluent. This yielded 7.33 g of brown solid. Recrystallization from ether/petroleum ether (1:3) yielded a yellowish crystal (m.p. 80°–83.5° C.) which appeared pure by TLC ($CH_2Cl_2$, Rf=0.43; EtOAc, Rf=0.60). Further elution of the column yielded the 3-isomer in 17% yield.

ANALYSIS: Calculated for $C_{18}H_{14}FNO$: 77.40% C; 5.05% H; 5.02% N. Found: 77.51% C; 5.06% H; 4.88% N.

EXAMPLE 3

1-[(2-Fluorophenyl)phenylmethyl]pyrrol-2-yl chloromethyl ketone

A cooled mixture of chloroacetonitrile (11.3g) and $ZnCl_2$ (10.2 g) in 10 ml of diethyl ether was saturated with gaseous hydrochloric acid. A solution of 1-[(2-fluorophenyl)phenylmethyl]pyrrole (18.8 g) in 200 ml of ethyl ether was added and this was stirred for 6 hours. The resulting solid was collected, added to water and heated at 95° C. for 2 hours. This was then cooled and extracted with ethyl ether and the organics were dried (saturated NaCl, $MgSO_4$) and concentrated to give 20.4 g of a yellow oil, a portion of which was crystallized to give a white solid, mp 86°–91° C.

EXAMPLE 4

1-[(2-Fluorophenyl)phenylmethyl]pyrrol-2-yl dimethylaminomethyl ketone hydrochloride To a solution of methanol saturated with dimethylamine was added 1-[(2-fluorophenyl)phenylmethyl]pyrrol-2-yl chloromethyl ketone (20.39 g in 500 ml of MeOH). This was heated at an oil bath temperature of 85° C. and stirred for 2 hours.

The reaction mixture was cooled, concentrated and added to water (pH adjusted to about 12). This was then stirred for 15 minutes and extracted with ether (3×). The combined organics were washed with water (1×) and dried (sat. NaCl, $MgSO_4$). This was filtered and concentrated to 18.76 g of oil.

A portion of this was made into its hydrochloride salt. Recrystallization from ethanol/isopropyl ether afforded a white solid of analytical purity, m.p. 219°–221° C.

ANALYSIS:
Calculated for $C_{21}H_{21}ClFN_2O\cdot HCl$: 67.64% C; 5.95% H; 7.51% N. Found: 67.70% C; 6.07% H; 7.48% N.

EXAMPLE 5

α-(Dimethylamino)methyl-1-[(2-fluorophenyl)phenylmethyl]-1H-pyrrole-2-methanol oxalate To a suspension of $NaBH_4$ (3.53 g) in 150 ml of isopropanol was added 1-[(2-fluorophenyl)phenylmethyl]-pyrrol-2-yl dimethylaminomethyl ketone (13.79 g dissolved in 200 ml of isopropanol). The mixture was heated to reflux and stirred for 6 hours.

The reaction mixture was cooled and added to 400 ml of iced $H_2O$ and stirred. This was extracted several times with $CH_2Cl_2$ and the organics were dried (sat. NaCl, $MgSO_4$). This was filtered and concentrated to yield a yellow oil. HPLC (high performance liquid chromatograph) separation of the alcohol yielded 11.54 g of a pure yellow solid, mp 75.5°–78° C. A portion of this was made into its oxalate salt and recrystallized from ethanol/isopropyl ether to afford analytically pure light yellow crystals, m.p. 141°–143.5° C.

ANALYSIS Calculated for $C_{21}H_{23}FN_2O\cdot C_2H_2O_4$: 64.48%C; 5.88%H; 6.54%N. Found: 64.37% C; 6.00% H; 6.49% N.

EXAMPLE 6

α-(1-Methyl-4-piperidinyl)-1-[(2-fluorophenyl)phenylmethyl]-1H-pyrrole-2-methanol To magnesium turnings (0.53 g) in 10 ml of 10% $Et_2O$/THF (tetrahydrofuran) solution, was added a few drops of 1,2-dibromoethane followed by a few drops of a 4-chloro-1-methyl piperidine solution (2.79 g in 15 ml of 10% $Et_2O$/THF).

Reaction was initiated by heat and the rest of the 4-chloro-1-methylpiperidine solution was added over 20 minutes. The mixture was stirred at reflux for one hour during which time the solution clouded up.

The heat was removed and a solution of 1-[(2-fluorophenyl)phenylmethyl]pyrrole-2-carboxaldehyde (2.92) in 30 ml of 10% $Et_2O$/THF was added dropwise. The mixture cleared up and was refluxed for 1 hour. At this time, TLC showed completion of the reaction.

The mixture was concentrated to about ½ volume and added to 150 ml of iced $NH_4Cl$ solution. The mixture was stirred for 20 minutes and extracted with ether. The ether layer was washed (2 × $H_2O$; 1×sat. $NH_4Cl$) and dried (sat. NaCl, anhydrous $MgSO_4$).

The mixture was filtered and concentrated to a yellow fibrous solid which yielded 3.76 g of a slightly yellowish solid upon tituration with ether/petroleum ether (1:3). Recrystallization from hexane/ethanol yielded slightly yellow crystals, m.p. 121.5°–124° C.

ANALYSIS: Calculated for $C_{24}H_{27}FN_2O$: 76.16% C; 7.19% H; 7.40% N. Found: 75.91% C; 7.02% H; 7.48% N.

EXAMPLE 7

α-(1-Benzyl-4-piperidinyl)-1-[(2-fluorophenyl)phenylmethyl]-1H-pyrrole-2-methanol oxalate To magnesium turnings (1.51 g) in 30 ml of 10% $Et_2O$/THF was added a few drops of 1,2-dibromoethane, followed by a few drops of a solution of 4-chloro-1-benzylpiperidine (131.0 g in 80 ml of 10% $Et_2O$/THF).

The reaction mixture was heated and the rest of the 4-chloro-1-benzylpiperidine solution was added slowly. The mixture was refluxed for three hours during which time it turned cloudy.

The heat was removed and a solution of 1-[2-fluorophenyl)phenylmethyl]pyrrole-2-carboxaldehyde 17.32 g in 150 ml of THF was slowly added. The solution cleared up a short time later and this mixture was stirred at reflux for 3 hours.

The reaction was cooled and quenched in 400 ml of iced $NH_4Cl$ solution. This was extracted with $Et_2O$ (4×). The organics were washed with $H_2O$ and dried with sat. NaCl and $MgSO_4$.

The mixture was filtered and the filtrate concentrated to an orange oil and the alcohol was separated via HPLC to yield 9.89 g of a pure yellow oil. A portion of this was made into the oxalate salt with ethereal oxalic acid yielding a slightly yellow solid which was recrystallized from isopropyl ether/ethanol to yield an analytically pure white solid, mp=yellows at 100° C.; decomposes at 130° C.

ANALYSIS: Calculated for $C_{30}H_{31}FN_2O\cdot C_2H_2O_4$: 70. 57% C; 6.11% H; 5.14% N. Found: 70.69% C; 6.39% H; 4.75% N.

EXAMPLE 8

11-Dimethylaminomethyl-5-phenyl-5H,11H-pyrrolo[2,1-c][1,4]benzoxazepine hydrochloride To a suspension of sodium hydride (obtained from 1.55 g of 50% suspension in mineral oil, washed with hexane) in 100 ml of 20% DMF/benzene, was added a solution of α-[(dimethylamino)methyl]-1-[(2-fluorophenyl)phenylmethyl]-1H-pyrrole-2-methanol (8.80 g in 125 ml of 20% DMF/benzene).

The mixture was heated to reflux and stirred for 3.5 hrs. After cooling, the mixture was added to 400 ml of iced H$_2$O and stirred for 20 min. This was then extracted with ethyl acetate and the combined organics were dried with sat. NaCl and anhydrous MgSO$_4$.

The mixture was filtered and the filtrate concentrated to an orange oil. The two isomers were separated via HPLC (hexane/EtOAc/Et$_2$NH; 80:20:2) to yield 6.21 g of a light orange solid (m.p. 82°–87° C.) and 1.49 g of a light yellow solid (m.p. 119°–122.5° C.). The major isomer A was dissolved in ether and ethereal HCl was added to give 6.7 g of the hydrochloride salt. A portion of the hydrochloride salt was recrystallized from ethanol/isopropyl ether to give an analytically pure white solid, m.p. 205°–205.5° C. Similar treatment of the minor diastereoisomer (B) gave the hydrochloride salt which on recrystallization from ethanol/isopropyl ether gave a light tan solid, mp 117.5°–119.5° C.

ANALYSIS: Calculated for C$_{21}$H$_{22}$N$_2$O·HCl: 71.08% C; 6.53% H; 7.89% N. Found: (A)·HCl 70.86% C; 6.61% H; 7.80% N;

(B)·HCl 70.90% C; 6.63% H; 7.59% N.

EXAMPLE 9

11-(N-Ethoxycarbonyl-N-methylaminomethyl)-5-phenyl-5H,11H-pyrrolo[2,1-c][1,4]benzoxazepine To a mixture of 11-dimethylaminomethyl-5-phenyl-5H,11H-pyrrolo[2,1-c][1,4]benzoxazepine 9.92 g) and potassium carbonate (4.28 g) in 150 ml of benzene was added ethyl chloroformate (5.9 ml). This was heated at 65° C. for 6 hours, then added to water and extracted with ethyl ether (4×). The combined organics were washed with water, dried and concentrated to give 10.5 g of an oil which was used without further purification.

EXAMPLE 10

11-Methylaminomethyl-5-phenyl-5H,11H-pyrrolo[2,1-c][2,4]benzoxazepine hydrochloride To a solution of 11-[(N-ethoxycarbonyl-N-methylamino)methyl]-5-phenyl-5H,11H-pyrrolo[2,1-c][1,4]benzoxazepine (10.4 g in 100 ml of EtOH) was added 75 mil of 20% NaOH. This was refluxed with vigorous stirring for 48 hours. The reaction mixture was then extracted with ethyl acetate and dried (sat. NaCl, MgSO$_4$).

This was filtered and concentrated to yield 10.2 g of a dark oil. The amine was separated via column chromatography yielding 3.45 g of a tan solid. The HCl salt was formed using ethereal-HCl and recrystallized from methanol/ethyl ether to yield a light yellow solid of analytical purity, mp 235°–236.5° C.

ANALYSIS: Calculated for C$_{20}$H$_{20}$N$_2$O·HCl: 70.48% C; 6.21% H; 8.22% N. Found: 70.27% C; 6.18% H; 8.14% N.

EXAMPLE 11

11-(1-Methyl-4-piperidinyl)-5-phenyl-5H,11H-pyrrolo[2,1-c][1,4]benzoxazepine

To a suspension of sodium hydride (obtained from 0.764 g of 50% suspension in oil, washed with hexanes) in 20 ml of benzene, was added a solution of α-(1-methyl-4-piperidinyl)-1-[(2-fluorophenyl)phenylmethyl]-1H-pyrrole-2-methanol (4.8 g) dissolved in 50 ml of 20% DMF/benzene.

The mixtures was then stirred at 80° C. for 3 hours at which time TLC (20% DMF/EtOAc) showed completion of the reaction. The mixture was concentrated and added to 250 ml of H$_2$O. The mixture was stirred for 20 minute and extracted with ether. The organic phase was washed with water (2×) and dried (sat. NaCl, anhydrous MgSO$_4$).

The mixture was filtered and the filtrate concentrated to a yellow oil which solidified to a white solid upon trituration with ether/petroleum ether (1:3) (3.74 g). Recrystallization from acetonitrile yielded white crystals, m.p. 183°–186° C.

ANALYSIS: Calculated for C$_{24}$H$_{26}$N$_2$O: 80.41% C; 7.31% H; 7.81% N Found: 80.52% C; 7.30% H; 7.82% N.

EXAMPLE 12

11-(1-Benzyl-4-piperidinyl)-5-phenyl-5H,11H-pyrrolo[2,1-c][1,4]benzoxazepine oxalate To a suspension of sodium hydride (obtained from 0.57 g of 50% suspension in oil, washed with hexane) in 40 ml of 20% DMF/benzene, was added a solution of α-(1-benzyl-4-piperidinyl)-1-[(2-fluorophenyl-phenyl-methyl]-1H-pyrrole-2-methanol (5.05 g in 60 ml of 20% DMF/benzene).

The mixture was heated to reflux and stirred for 4 hrs. After cooling, the mixture was concentrated to half volume and added to water. The resultant mixture was stirred for 15 minutes and then extracted with ethyl ether and the organics were dried (sat. NaCl, MgSO$_4$).

The mixture was filtered and the filtrate concentrated to an orange oil. This was taken up in ether and an ethereal solution of oxalic acid was added to form the oxalate salt (3.93 g white solid).

This was recrystalized twice from ethyl acetate/methanol to yield an analytically pure white solid, mp 176°–180° C.

ANALYSIS: Calculated for C$_{30}$H$_{33}$N$_2$O·C$_2$H$_2$O$_4$: 73.26% C; 6.15% H; 5.34% N. Found: 73.09% C; 6.17% H; 5.33% N.

We claim:

1. A hypotensive composition comprising an effective blood pressure lowering amount of a compound having the formula

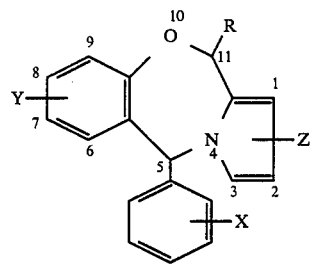

where X and Y are each independently hydrogen, loweralkyl, halogen or trifluoromethyl; Z is hydrogen or 2- or 3-Cl, Br, I, CHO or CH=CR$_1$R$_2$ where R$_1$ and R$_2$ are each independently hydrogen or loweralkyl; R is hydrogen, —(CH$_2$)$_n$NR$_3$R$_4$ or

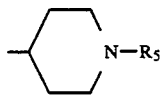

where n is 1, 2 or 3, R$_3$ is loweralkyl, and R$_4$ is hydrogen or loweralkyl, or alternatively the group -NR$_3$R$_4$ as a whole is

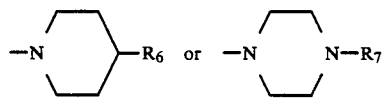

where R$_6$ is loweralkyl,

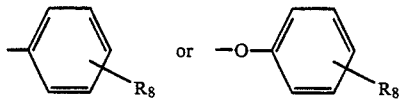

and R$_7$ is loweralkyl or

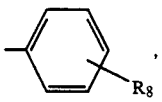

R$_8$ being hydrogen, loweralkyl, halogen, trifluoromethyl or methoxy; and R$_5$ is hydrogen, loweralkyl or arylloweralkyl, or a pharmaceutically acceptable acid addition salt thereof and a suitable carrier therefor.

2. A method of reducing blood pressure in a patient in need of blood pressure reduction which comprises administration of an effective amount of a compound having the formula,

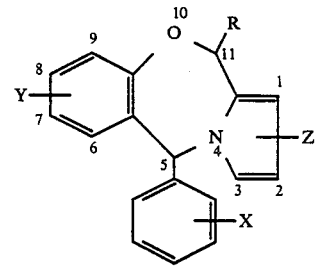

where X and Y are each independently hydrogen, loweralkyl, halogen or trifluoromethyl; Z is hydrogen or 2- or 3-Cl, Br, I, CHO or CH=CR$_1$R$_2$ where R$_1$ and R$_2$ are each independently hydrogen or loweralkyl; R is hydrogen, —(CH$_2$)$_n$NR$_3$R$_4$ or

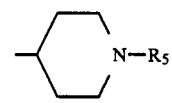

where n is 1, 2 or 3, R$_3$ is loweralkyl, and R$_4$ is hydrogen or loweralkyl, or alternatively the group —NR$_3$R$_4$ as a whole is

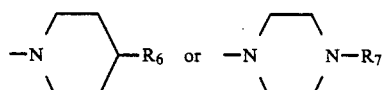

where R$_6$ is loweralkyl,

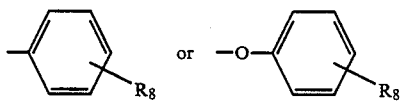

and R$_7$ is loweralkyl or

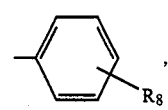

R$_8$ being hydrogen, loweralkyl, halogen, trifluoromethyl or methoxy; and R$_5$ is hydrogen, loweralkyl or arylloweralkyl, or a pharmaceutically acceptable acid addition salt thereof.

* * * * *